United States Patent [19]

Van Gompel et al.

[11] Patent Number: 4,938,753
[45] Date of Patent: Jul. 3, 1990

[54] SEAM CONSTRUCTION IN A DISPOSABLE TRAINING PANT, INCONTINENCE GARMENT, OR DIAPER

[75] Inventors: Paul T. Van Gompel, Hortonville; Jody D. Suprise, Neenah; Robert J. Schleinz, Appleton, all of Wis.

[73] Assignee: Kimberly-Clark Corporation, Neenah, Wis.

[21] Appl. No.: 372,496

[22] Filed: Jun. 27, 1989

Related U.S. Application Data

[63] Continuation of Ser. No. 133,759, Dec. 16, 1987, abandoned.

[51] Int. Cl.$^5$ ............................................. A61F 13/16
[52] U.S. Cl. ................................. 604/385.2; 604/396
[58] Field of Search ............................. 604/396, 385.2

[56] References Cited

U.S. PATENT DOCUMENTS

| | | |
|---|---|---|
| 2,102,359 | 12/1937 | Frieman . |
| 2,166,012 | 7/1939 | Maida . |
| 2,252,019 | 8/1941 | Meinecke et al. . |
| 2,252,992 | 8/1941 | Steiner . |
| 2,397,641 | 4/1946 | Blair . |
| 2,435,945 | 2/1948 | Redmond . |
| 2,538,596 | 1/1951 | Sheridan . |
| 3,087,495 | 4/1963 | Hart . |
| 3,098,484 | 7/1963 | Younger ............... 604/396 |
| 3,142,301 | 7/1964 | Erteszek . |
| 3,368,563 | 2/1968 | Scheier ............... 604/396 |
| 3,386,446 | 6/1968 | Sloan ............... 2/407 |
| 3,397,696 | 8/1968 | Rickard . |
| 3,530,859 | 9/1970 | Heimowitz ............... 604/386 |
| 3,613,687 | 10/1971 | Kennedy . |
| 3,687,141 | 8/1972 | Matsuda ............... 604/396 |
| 3,768,481 | 10/1973 | Shibata . |
| 3,882,871 | 5/1975 | Taniguchi . |
| 4,031,568 | 6/1977 | Huff . |
| 4,205,679 | 6/1980 | Repke et al. . |
| 4,355,425 | 10/1982 | Jones et al. . |
| 4,425,128 | 1/1984 | Motomura . |
| 4,427,408 | 1/1984 | Karami et al. . |
| 4,522,853 | 6/1985 | Szonn et al. . |
| 4,534,769 | 8/1985 | De Jonckheese et al. . |
| 4,610,680 | 9/1986 | La Fleur . |
| 4,619,649 | 10/1986 | Roberts . |
| 4,655,760 | 4/1987 | Morman et al. . |
| 4,690,681 | 9/1987 | Haunschild et al. . |
| 4,695,279 | 9/1987 | Steer . |

FOREIGN PATENT DOCUMENTS 1520740  8/1978  United Kingdom .

Primary Examiner—C. Fred Rosenbaum
Assistant Examiner—Sharon Rose
Attorney, Agent, or Firm—Douglas L. Miller

[57] ABSTRACT

A seam construction for an absorbent article comprises a layered composite portion of the absorbent article including a liquid pervious liner, a liquid impervious outer cover, and an absorbent medium therebetween. A pair of stretchable members are joined to the layered composite portion between respective side portions of the outer cover and the liner. The stretchable side members also extend outwardly beyond the opposite side portions of the outer cover and liner. The layered composite portion and each stretchable member form a seam construction that is resistant to liquid leakage and that provides a gentle transition between the layered composite portion and the stretchable members.

37 Claims, 10 Drawing Sheets

SEAM CONSTRUCTION IN A DISPOSABLE TRAINING PANT, INCONTINENCE GARMENT, OR DIAPER

This is a continuation application of application Ser. No. 133,759 filed on Dec. 16, 1987, now abandoned.

BACKGROUND OF THE INVENTION

This invention pertains to an absorbent article, and more particularly to seam constructions in an absorbent article for use as a child'training pant, adult incontinence garment, baby diaper and the like.

Currently, disposable absorbent articles find widespread use for infant care and adult incontinence care, and have generally replaced the use of reusable cloth absorbent articles, such as cloth diapers. The typical disposable absorbent article is a three-layered composite structure comprising a liquid-permeable bodyside liner, a liquid-impermeable outer cover and an absorbent batt disposed between the bodyside liner and the outer cover. Materials now in general use for the three principal elements of a disposable absorbent article include various types of nonwoven fabrics for the bodyside liner, a thin thermoplastic film for the outer cover and cellulosic fluff for the absorbent batt.

As one type of a disposable absorbent article, diapers presently on the market are flat open-sided garments that are intended to be fitted about an infant while lying down. A diaper is meant for use when the child is young and dependent upon a parent for fitting the diaper on the child.

The popularity of disposable diapers has led us to believe there is a demand for a disposable training pant that can be used when a child grows out of a diaper. Diapers are typically used with infants up to about 15 months old. When a child reaches an age in the range of about 15 to 30 months, a parent generally desires to start toilet training so the child can become independent of the parent. The training pant is intended for use when the child has reached an age at which he or she is ready to graduate to an underpant type of garment as a replacement for disposable diapers previously used. Thus, a suitable training pant must be a garment having closed sides so that a child can raise and lower the garment as necessary without requiring the aid of a parent. At the same time, a training pant must provide features of liquid and solid absorbency and prevent leakage of the waste fluids.

As another type of a disposable absorbent article, some of the currently-used incontinence products for adults and older children have been found unsatisfactory due to their bulkiness and ineffectiveness in leakage prevention. Many of these garments are formed by folding flat sheets into a diaper-like folded structure that is bulky and has gaps between the body and article, particularly in the crotch portion.

One of the important performance characteristics required of these articles is the prevention of leakage of liquid and waste matter from the absorbent batt through the seam of the article. Although one solution is to increase the amount of absorbent material, this has the undesirable effect of creating a bulky crotch area. Other attempted solutions have not been totally successful in preventing this type of leakage.

SUMMARY OF THE INVENTION

In one form of the invention, there is provided a seam construction in an absorbent article comprising a layered composite portion including a top layer, a middle layer, and a bottom layer; and a pair of stretchable members being joined to the layered composite portion between respective opposite side portions of the top layer and the bottom layer. The stretchable members extend outwardly beyond the opposite side portions of the top and the bottom layers, whereby the layered composite portion and each stretchable member form a seam construction that is resistant to liquid leakage and that provides a gentle transition between the layered composite portion and the stretchable members.

BRIEF DESCRIPTION OF THE DRAWINGS

The above-mentioned and other features and objects of this invention and the manner of attaining them will become more apparent, and the invention itself will be better understood by reference to the following description of the invention taken in conjunction with the accompanying drawings, wherein.

DETAILED DESCRIPTION

Figure 1:
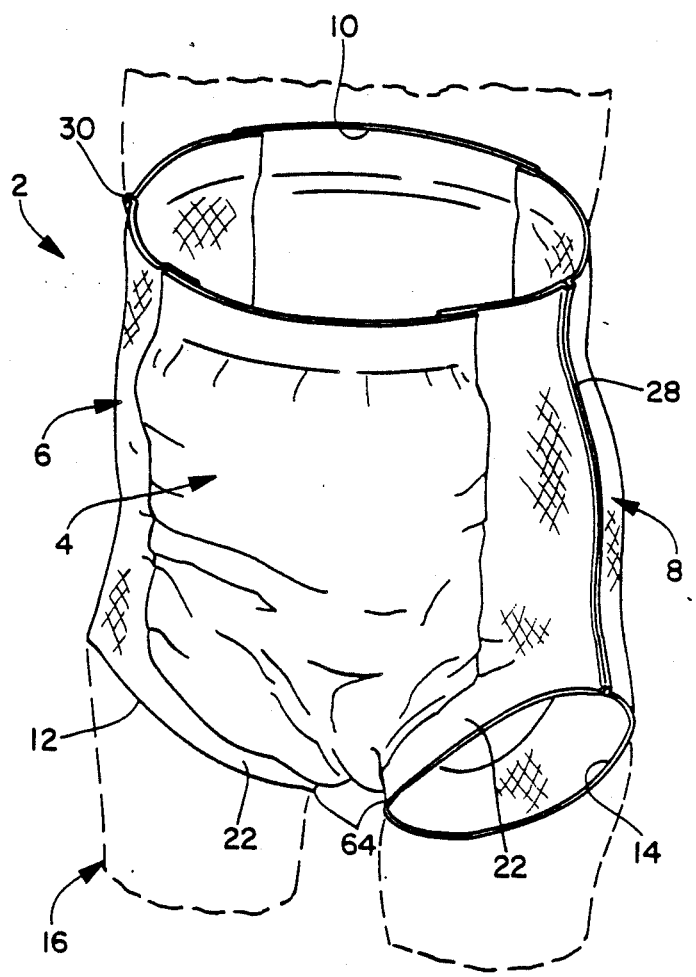
FIG. 1 is a perspective view of a training pant or incontinence garment as it would appear being worn on a wearer indicated in dashed lines.
Figure 2:
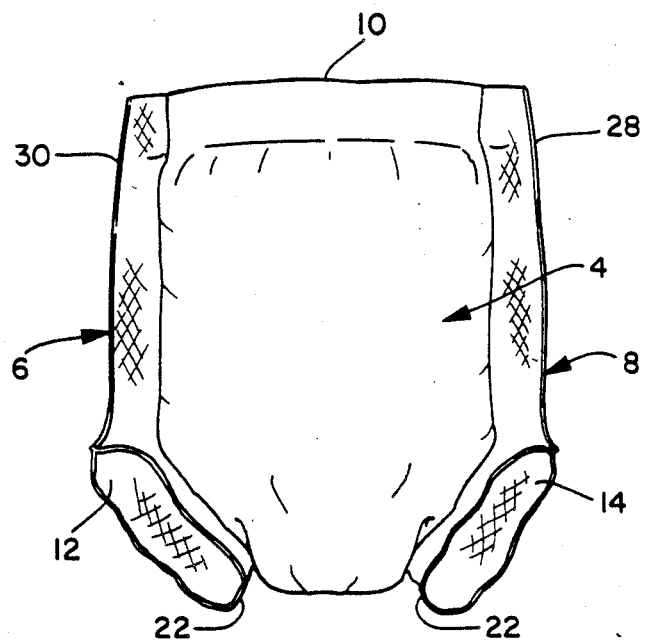
FIG. 2 is a front elevational view of the pant or garment in FIG. 1.
Figure 4:
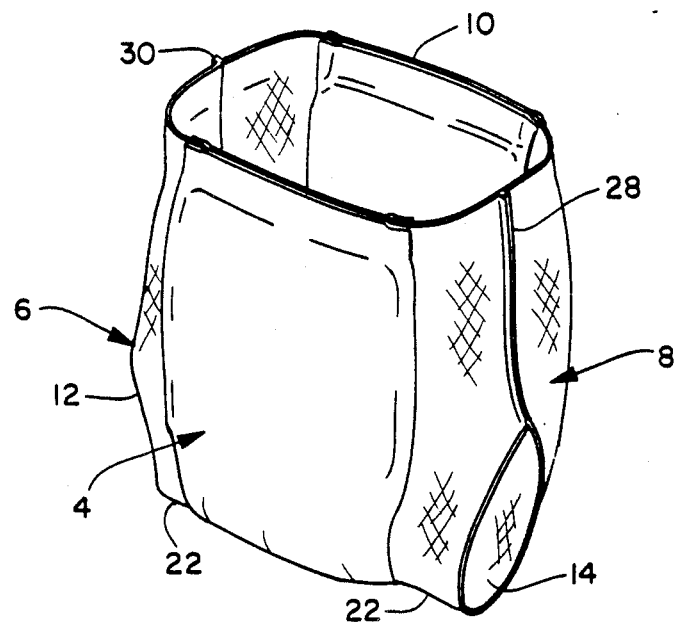
FIG. 4 is a perspective view of the pant or garment of FIG. 1.

Referring to FIGS. 1, 2 and 4, there is illustrated one embodiment of a pant or garment designated absorbent garment 2. Garment 2 generally comprises waste containment section 4 and two elastic or stretchable side panels 6, 8 defining a waist opening 10 and a pair of leg openings 12, 14. The total surface area of both side panels 6, 8 comprise about 20% to about 80% of the total surface area of garment 2, preferably about 25% to about 50%, and more preferably about 35% to about 45%. FIG. 1 illustrates absorbent garment 2 fitted on a wearer's torso portion 16 in dashed lines.

Figure 5:
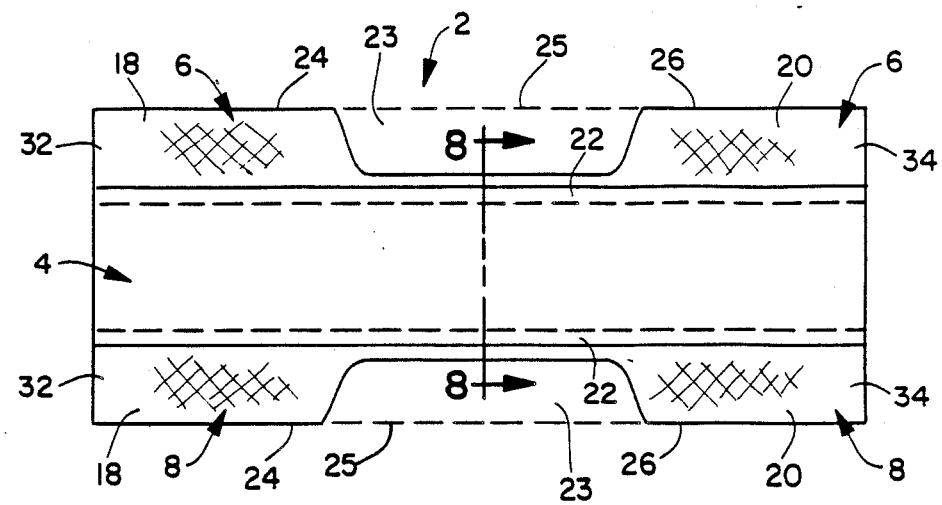
FIG. 5 is a top plan view of the pant or garment of FIG. 1 in a flat condition with leg cut-outs before the seams are joined.

Referring now to FIG. 5, absorbent garment 2 is illustrated in a two-dimensional or planar configuration it assumes during the manufacturing process. Elastic side panels 6, 8 are joined to waste containment section 4, and each side panel 6, 8 includes relatively wide end portions 18, 20 being joined by relatively narrow intermediate portions 22, thereby forming leg cut-outs 23. When the remote edges 24 of respective end portions 18 are joined to remote edges 26 of respective end portions 20 to form seams 28, 30 (FIG. 1), stretchable intermediate portions 22 provide elasticity for leg openings 12, 14. Similarly, when end portions 18 are joined to end portions 20, remote end segments 32 of end portions 18 and remote end segments 34 of end portions 20 provide elasticity to waist opening 10. Generally, each side panel will have a length of about 12 inches to about 30 inches, and a width from about 1 inch to about 6 inches. The total garment length is generally the same as the total length of a side panel.

Hereafter, the terms "elasticity," "stretchability," and "elongation" will be interchangeably used to describe the properties of various materials. The meaning of these three words is intended to be the same, and that is that the material can be stretched and, upon relaxing, will tend to resume its original shape.

If desired, narrow intermediate portions 22 can be eliminated, i.e., not manufactured into garment 2, so that end portions 18, 20 extend as one integral portion along dashed lines 25. Portions 18, 20 would still be joined as described above to form leg openings 12, 14. That is, the intermediate portions of portions 18, 20 indicated by dashed lines 25 would not be bonded.

As mentioned earlier, side panels 6, 8, which includes end portions 18, 20 and intermediate portion 22, have elastic or stretchable properties. Side panels 6, 8 can be made of a single layer of woven or nonwoven elastic or stretchable material, such as block copolymers of polystyrene, polyisoprene or polybutadiene copolymers of ethylene, natural rubbers, urethanes, Kratons and coextrusions/blends of the aforementioned. Other examples of suitable elastomeric materials include copolymers of ethylene, EVA (ethylene-vinyl acetate), EEA (ethylene-ethyl acetate), EAA (ethylene-acrylic acid) and EMA (ethylene-methyl acrylate) and various percent blends of the copolymers of ethylene with polypropylene. Co-extruded composites of EVA (ethylene-vinyl acetate), EEA (ethylene-ethyl acetate), EAA (ethylene-acrylic acid) and EMA (ethylene-methyl acrylate) and polypropylene at various percents or mil thicknesses could also be used as the elastic material. Also, elastomeric staple integrated composites where staple fibers such as polypropylene, polyester, cotton or any other suitable staple fiber are integrated into an elastomeric meltblown web. Stretchable side panels 6, 8 can also be a film of elastomeric material.

The above elastomeric materials may be formed by any suitable processes, such as film extrusion, spunbond process, meltblown process and the like.

Figure 6:
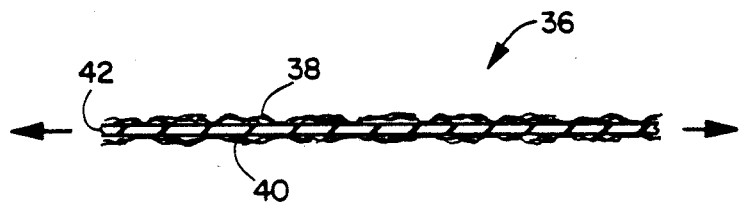
FIG. 6 is a fragmentary, side cross-sectional view of a stretch-bonded laminate in the stretched condition.
Figure 7:
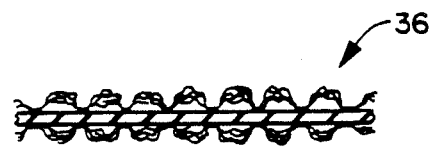
FIG. 7 is a fragmentary, side cross-sectional view of the stretch-bonded laminate of FIG. 6 in a relaxed condition.

Side panels 6, 8 can also be a stretch-bonded laminate that may have elasticity in all directions, and may be breathable, i.e., is pervious to vapors, but impervious to liquids. FIGS. 6 and 7 illustrate a stretch-bonded laminate 36 in the stretched and relaxed conditions, respectively. Stretch-bonded laminate 36 generally comprises an outer layer 38, an inner bodyside layer 40 and an elastic or stretchable layer 42 disposed between layers 38, 40. Although 38, 40 are described as outer and inner, respectively, they can be made of the same materials, and thus be interchangeable.

Layers 38, 40 can be made of any woven or nonwoven material, and are preferably made of a nonwoven fibrous material. Examples of nonwoven fibrous material include variously bonded polyolefin fibers such as thermally-bonded polypropylene, polyethylene, polyester; spunbonded polypropylene, spunbonded polyethylene or blends thereof; meltblown polypropylene, meltblown polyethylene or blends thereof; bonded carded webs of synthetic or natural fibers or blends thereof; extruded films of thermoplastic materials; and the like. Naturally, copolymers of polyolefin or other material fibers may also be utilized.

Elastic or stretchable layer 42 can be a meltblown or film of block or graft copolymers such as butadiene, isoprene, styrene, ethylene-methyl acrylate, ethylene-vinyl acetate, ethylene-ethyl acrylite or blends thereof. One preferred elastomeric is a block copolymer of styrene-ethylbutadiene-styrene. Other types of materials of which elastic layer 42 can be made are the Kraton G series from The Shell Chemical Company such as Kraton G-1650, Kraton G-1652, Kraton GX-1657 and preferably Kraton G-2740X. Also, the Kraton D series can be used, as well as polyester elastomeric materials, polyurethane elastomeric materials and polyamide elastomeric materials.

It should be pointed out at this point that the stretchable or elastomeric materials of which side panels 6, 8 are made can also be used for layer 42, and the just-described stretchable or elastomeric materials of which layer 42 can be made may also be used to make side panels 6, 8.

Typically, a stretch-bonded laminate is made by stretching the elastic or stretchable layer 42 to a selected elongation; placing a nonstretched layer, such as layer 38 or 40 or both, on the stretched layer 42; bonding the layers together and allowing the layers to relax so that layer 42 gathers the other layers.

Figure 8:
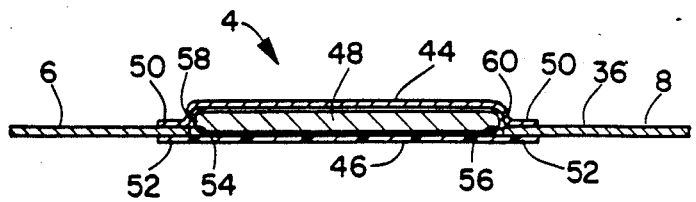
FIG. 8 is a sectional view of FIG. 5 taken along line 8—8 and viewed in the direction of the arrows.

Referring now to FIG. 8, which is a cross-section through FIG. 5, the attachment of waste containment section 4 with side panels 6, 8 is illustrated. Waste containment section 4 generally comprises a fluid-pervious bodyside liner 44, a liquid-impervious outer cover 46 and an absorbent medium 48 between liner 44 and cover 46. Outer cover 46 can be a woven or nonwoven material, film, or a film-coated nonwoven material comprising cast or blown films of polyethylene, polypropylene, polyester or blends thereof. Outer cover 46 may also be a composite of a bonded carded or spunbonded or meltblown material, for example, a bonded carded-film composite, or a spunbonded-meltblown composite of thermoplastic material, or a spunbonded-meltblown-spunbonded thermoplastic material, wherein the spunbonded layer can provide a cloth-like texture and the meltblown layer can provide liquid impermeability. Materials of which outer cover 46 can be made include nonwovens having a high basis weight, such as about 0.4 ounces per square yard, about 10 grams per square meter or basis weights greater than the aforementioned. Outer cover 46 can also be extruded films of polyolefin polymers or copolymers or other thermoplastic materials. Generally outer cover 46 will have a length from about 12 inches to about 30 inches, and a width from about 3 inches to about 20 inches.

Bodyside liner 44 can be a woven material, or a nonwoven material such as any flexible porous sheet of polyolefin fibers, such as polypropylene or polyethylene or polyester fibers; a web of spunbonded polypropylene or polyethylene or polyester fibers; a web of rayon fibers; a bonded carded web of synthetic or natural fibers or blends thereof. Liner 44 can also be an apertured plastic film. Liner 44 generally will have a length from about 12 inches to about 30 inches, and a width from about 3 inches to about 20 inches.

Absorbent medium 48 can be made of wood pulp fluff or a mixture of wood pulp fluff and a superabsorbent material, or a wood pulp fluff integrated with a thermoplastic absorbent material treated with a surfactant. Thermal binders, such as Pulpex ® can be used in blends or layering with the fluff and superabsorbent. Medium 48 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins. Medium 48 generally will have a length from about 12 inches to about 30 inches, and a width from about 3 inches to about 20 inches.

As illustrated in FIG. 8, outer cover 46 and bodyside liner 44 sandwich absorbent medium 48, which is preferably adhered only to outer cover 46 by any suitable adhesive or other means. Alternatively, absorbent medium 48 could be joined to bodyside liner 44 or both bodyside liner 44 and outer cover 46. The longitudinal edge portions 50 of bodyside liner 44 and the longitudinal edge portions 52 of outer cover 46 also sandwich respective edge portions of side panels 6, 8 to join them to waste containment section 4. Side panels 6, 8 can be joined or adhered between respective edge portions 50, 52 by heat sealing, ultrasonic sealing, adhesive sealing or by other conventional means, such as stitching and the like.

As illustrated in FIG. 8, side panels 6, 8 have respective panel inner sides 54, 56 that are illustrated as being just slightly spaced apart from respective absorbent sides 58, 60. One of the unique features of the present invention is the positional relationship between the panel inner sides 54, 56 and absorbent sides 58, 60. Depending on the degree of elasticity and the amount of gathering desired, the panel inner sides 54, 56 can be positioned at different distances from respective absorbent sides 58, 60. For example, panel inner sides 54, 56 can be in direct abutment against absorbent sides 58, 60 to provide maximum gathering, or panel inner sides 54, 56 can be spaced apart from respective absorbent sides 58, 60 as desired. A desired range of distances between panel inner sides 54, 56 and respective absorbent sides 58, 60 is 0 to about 2 inches. A preferred range is from 0 to about 1 inch, and a more preferred range is from 0 to about ½ inch. Alternatively, panel inner sides 54, 56 could overlap or extend over or under absorbent sides 58, 60.

When panel inner sides 54, 56 are in abutment against absorbent sides 58, 60, the effect is to provide additional seal against leakage, and allow for a more uniform transition from side panel to absorbent.

As the panel inner sides 54, 56 are spaced an increasing distance from absorbent sides 58, 60, the resulting effect is to allow additional flexibility to the leg gasketing at each leg opening.

Figure 9:
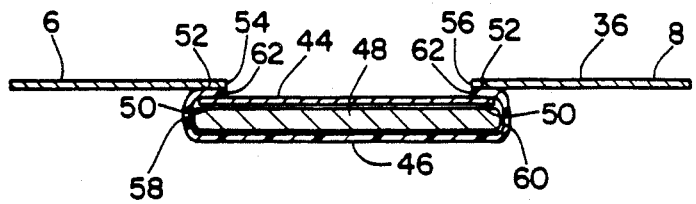
FIG. 9 illustrates a modification of the view of FIG. 8.

Referring to FIG. 9, there is illustrated a modification to the structure of FIG. 8. The longitudinal edge portions 50 of bodyside liner 44 terminate substantially at absorbent sides 58, 60. Longitudinal edge portions 52 of outer cover 46 overlap absorbent sides 58, 60 and edge portions 50 to form liquid-impervious baffles 62. Side panels 6, 8 are then joined on top of edge portions 52, which form baffles 62, such that edge portions 52 of outer cover 46 are joined between respective side panels 6, 8 and bodyside liner 44. As illustrated in FIG. 9, panel inner sides 54, 56 of side panels 6, 8 are substantially coincident with the remote ends of edge portions 52. If desired for better fluid control, baffles 62, which again are the overlapping edge portions 52 of outer cover 46, can extend further inwardly over bodyside liner 44 and beyond panel inner sides 54, 56, thereby creating larger baffles 62. By so extending baffles 62 toward the central portion of absorbent medium 48, there is a reduction in the amount of fluid flowback that may occur in both the longitudinal and transverse directions, thereby further reducing the chance of any fluid leakage about the leg openings 12, 14.

Figure 10:
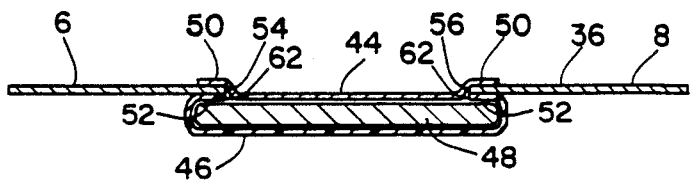
FIG. 10 illustrates a modification of the view of FIG. 8.

Referring to FIG. 10, another modification of FIG. 8 is illustrated. In this particular modification, edge portions 52 of outer cover 46 overlap only absorbent medium 48. Side panels 6, 8 are then attached to the top of edge portions 52, again which form baffles 62, and bodyside liner 44 is then attached to side panels 6, 8. As illustrated in FIG. 10, panel inner sides 54, 56 are substantially coincident with the ends of edge portions 52. However, edge portions 52, forming baffles 62, can extend further inwardly toward the center of absorbent medium 48, thereby providing greater protection against fluid flowback in both the longitudinal and transverse directions.

The percentage of overlap or coverage of absorbent medium 48 by baffles 62 can be 0 to about 99%, preferably about 10% to about 50%, and more preferably about 10% to about 20%.

As baffles 62 are disposed further inwardly toward the center of absorbent medium 48, panel inner sides 54, 56 of side panels 6, 8 can likewise be extended further inwardly before being joined to edge portions 52. The percent overlap or coverage of panel inner sides 54, 56 over absorbent medium 48 can be 0 to about 50%, preferably about 12%.

With reference to FIGS. 9 and 10, side panels 6, 8 alternatively can be attached to the bottom surface of outer cover 46.

As described above, waste containment section 4 of absorbent garment 2 is maintained in a snug-fitting, comfortable fashion against the wearer by elastic or stretchable side panels 6, 8. The effect of elastic or stretchable side panels 6, 8, which may also include the intermediate portion 22 extending about the inner portion of the wearer's legs, is to provide not only vertical forces that maintain the waste containment section 4 against the wearer's crotch area, but also inwardly directed horizontal force vectors against the hips and mid-section that hold or hug waste containment section 4 against the sides of the wearer, both before and after a void.

Figure 1A:
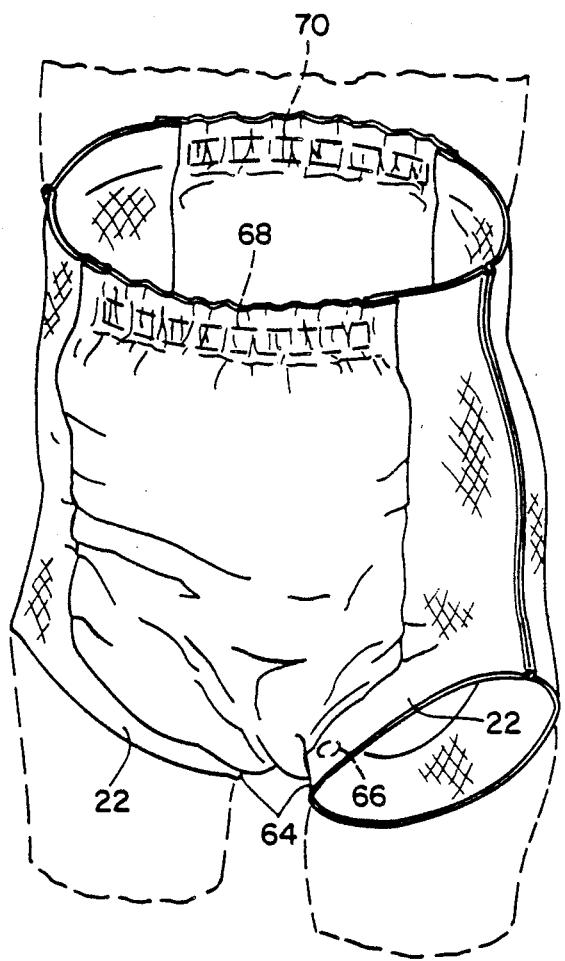
FIG. 1A is a perspective view of another pant or garment on a wearer indicated in dashed lines.
Figure 4A:
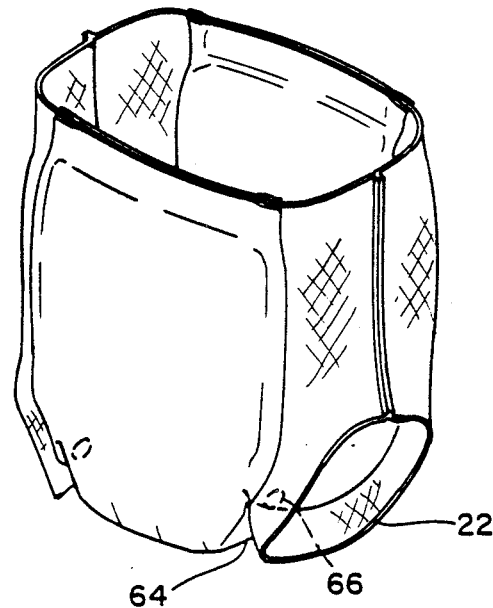
FIG. 4A is a perspective view similar to FIG. 4 illustrating a modification thereto.

Another unique feature of the present invention is illustrated in FIG. 1, 1A and 4A wherein intermediate portions 22 of elastic side panels 6, 8 form a pair of gussets 64. As illustrated in FIG. 1A, and in a more exaggerated manner in FIG. 4A, intermediate portions 22 are generally flat or planar in the transverse dimension, and curvilinear in the longitudinal dimension so as to conform to the wearer's leg. When absorbent garment 2 is properly fitted on the wearer, as illustrated in FIG. 1, each intermediate portion 22 tends to fold or tuck on itself to form a respective gusset 64 at the wearer's crotch area. This double tuck or gusset 64 provides additional gasketing about leg openings 12, 14, thereby further reducing the potential of fluid leakage, particularly during movement of the wearer.

The width or transverse dimension of each intermediate portion 22 is generally a function of the maximum width of its respective side panels 6, 8. The width of intermediate portion 22 can be about 5% to about 100% the maximum width of its side panel, preferably about 20% to about 80%, and more preferably about 30% to about 50%.

Gussets 64 can be preformed during the manufacturing of absorbent garment 2 by means of dots 66 of adhesive (FIGS. 1A and 4A). Dots 66 can also be formed by heat sealing, ultrasonic sealing or any other conventional means of attachment. The formation of gussets 64 with dots 66 can be made between the inner edge of portion 22 and the outer edge of portion 22, or between a transversely intermediate portion of portion 22 and an edge portion of waste containment section 4.

Figure 3:
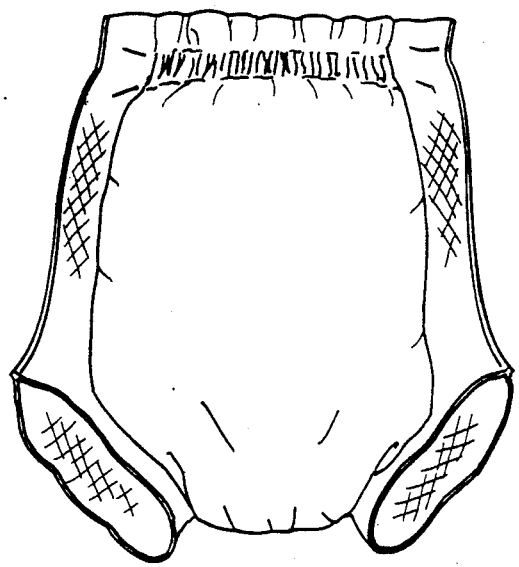
FIG. 3 is a front elevational view of the pant or garment in FIG. 1A.
Figure 5A:
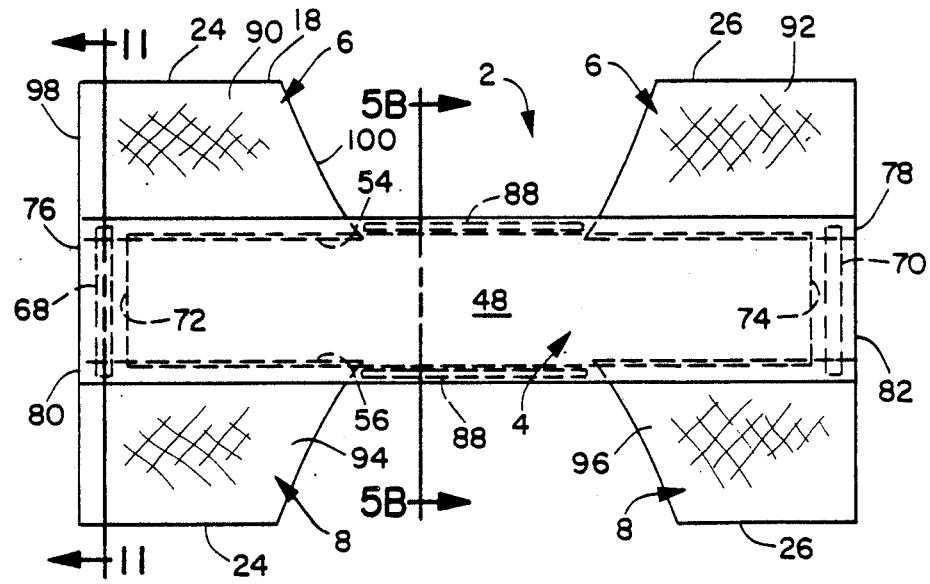
FIG. 5A illustrates a modification to the pant or garment in FIG. 5.

Referring now to FIGS. 1A, 3, and 5A, there is illustrated a modification of absorbent garment 2 in FIG. 1 by the addition of waist elastic 68 at the front of garment 2 and waist elastic 70 at the back of garment 2. Waist elastics 68, 70 can provide additional elastic stretch in the waist for better fit and additional leakage control.

Referring to FIG. 5A, waist elastics 68, 70 are illustrated with absorbent garment 2 in a two-dimensional or planar form before the construction of seams 28, 30. Ends 72, 74 of absorbent medium 48 terminate short of outer cover ends 76, 78 and bodyside liner ends 80, 82. Absorbent ends 72, 74 are spaced a distance from outer cover ends 76, 78 in the range of about ⅛ inch to about 2 inches. Generally, bodyside liner ends 80, 82 are substantially coincident with outer cover ends 76, 78, and the total length of the garment is measured between these ends. It may be that bodyside liner ends 80, 82 extend beyond outer cover ends 76, 78 and are folded over ends 76, 78 to form a skirt or fringe about waist opening 10. In this case, the total garment length is measured between ends 76, 78. Similarly, outer cover ends 76, 78 could extend beyond bodyside liner ends 80, 82 and be folded thereover, and the total garment length is measured between ends 80, 82.

Preferably, waist elastics 68, 70 are made of an activatable elastic material applied in an unstretched condition. Thereafter, waist elastics 68, 70 are activated, such as by heat, light, moisture or the like, so as to retract and become elastic. Types of these activatable elastic materials can be purchased from the Minnesota Mining and Manufacturing Company.

Each waist elastic 68, 70 can be a single ribbon of elastic material that is suitably adhered solely to bodyside liner 44, or to outer cover 46, or to both liner 44 and cover 46. A single ribbon of waist elastic 68 or 70 in the relaxed, attached condition has a length of about 2 inches to about 12 inches and a relaxed, attached width of about ¼ inch to about 2 inches. Generally, waist elastics 68, 70 will be adhered in a stretched condition, and in the stretched condition, each waist elastic 68, 70 will have a stretched length of about 2¼ inches to about 15 inches and a stretched width of about ⅛ inch to about 1⅞ inches. These parameters should provide a relaxed, attached length of about 50% to about 100% of the width of waste containment section 4.

Instead of each waist elastic 68, 70 being a single ribbon of elastic material, each may be comprised of a multiple strand of ribbons 69, 71 (FIG. 3) having a generally rectangular cross-section or ropes having a generally circular or arcuate cross-section. For example, if each waist elastic 68, 70 comprises multiple strands of ribbons, each of the ribbons in the strand will have a length similar to those for a single ribbon and a width from about ⅛ inch to about ¾ inch. If each waist elastic 68, 70 comprises multiple strands of rope elastics, each rope preferably will have a length similar as above and a width or diameter from about 0.04 inches to about 0.25 inches.

Waist elastics 68, 70 may be made of any suitable elastic material, such as those of which side panels 6, 8 or stretchable layer 42 can be made. Suitable adhesives for adhering waist elastics 68, 70 to absorbent garment 2 include hot melt adhesives, spray adhesives, self-adhering elastomeric materials and the like.

Figure 11:
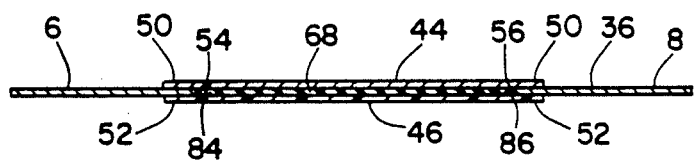
FIG. 11 is a sectional view of FIG. 5A taken along line 11—11 and viewed in the direction of the arrows.
Figure 12:
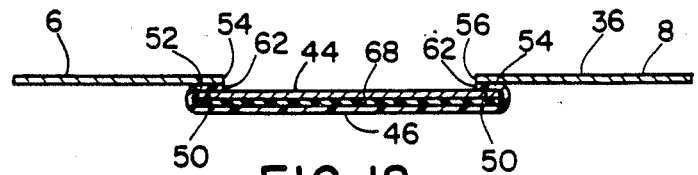
FIG. 12 illustrates a modification of the view of FIG. 11.
Figure 13:
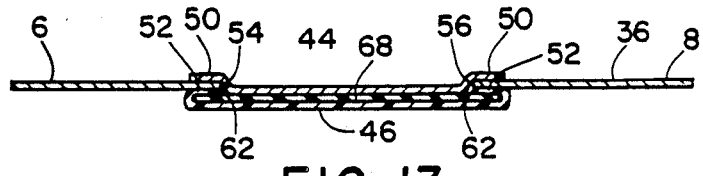
FIG. 13 illustrates a modification of the view of FIG. 11.

Referring now to FIGS. 11–13, the various seam configurations for waist elastics 68, 70 will be described. Since both waist elastics 68, 70 can be attached in a similar manner, only a description of waist elastic 68 will be made with the understanding that it also applies to waist elastic 70. In FIG. 11, waist elastic 68 is sandwiched between bodyside liner 44 and outer cover 46. Similarly, side panels 6, 8 are sandwiched between bodyside liner 44 and outer cover 46, with panel inner sides 54, 56 abutting against respective waist elastic sides 84, 86. The attachment of waist elastic 68 and panels 6, 8 to bodyside liner 44 and outer cover 46 can be made by heat sealing, ultrasonic sealing, adhesive sealing or any other suitable means. In FIG. 11, panel inner sides 54, 56 abut against respective waist elastic sides 84, 86 in order to provide a continuous stretchable or elastic effect about the periphery of waist opening 10. However, panel inner sides 54, 56 can be spaced from respective waist elastic sides 84, 86 in the range of 0 inches to about 2 inches. A preferred range is from 0 to about 1 inch, and a more preferred range is from 0 to about ½ inch. Also, side panel inner sides 54, 56 could overlap partially or completely waist elastics 68, 70 in that area between outer ends 76, 78 and absorbent ends 72, 74 (FIG. 5A).

Referring now to FIG. 12, the sides of waist elastic 68 and bodyside liner 44 are substantially coincident, and longitudinal edge portions 52 of outer cover 46 are folded to overlap longitudinal edge portions 50 of bodyside liner 44, thereby forming baffles 62. Side panels 6, 8 are then adhered to the exposed tops of baffles 62, such that panel inner sides 54, 56 are substantially coincident with the ends of baffles 62. Baffles 62 can be extended further inwardly toward the center portion of bodyside liner 44 to accommodate the modification described with reference to FIG. 9, wherein baffles 62 extend further inwardly of absorbent medium 48. The percentage of coverage or overlap of baffles 62 over waist elastics 68, 70 and bodyside liner 44 can be 0 to about 100%. Preferably, the coverage or overlap is about 5% to about 50%, and more preferably about 8% to about 13%.

Referring now to FIG. 13, longitudinal edge portions 52 of outer cover 46 overlap waist elastic 68 to form baffles 62, and side panels 6, 8 are then adhered to baffles 62. Bodyside liner 44 is disposed over waist elastic 68 and side panel inner sides 54, 56. Baffles 62 can extend over elastic 68 as described above with reference to FIG. 12.

Referring now to FIG. 5A, there is illustrated another modification of absorbent garment 2 wherein elastic intermediate portions 22 have been eliminated and leg elastics 88 substituted therefor. Leg elastics 88 may be made of the same or other described materials of which waist elastics 68, 70 can be made. Leg elastics 88 may be similarly adhered by one of those methods described for adhering waist elastics 68, 70. Each leg elastic 88 is preferably a single ribbon of elastic material having a relaxed, attached length of about 1 inch to about 18 inches, and a relaxed width of about ⅛ inch to about 3 inches, and an elongation of about 25% to about 350%. A preferred length is about 2 inches to about 9 inches and an elongation of about 30% to about 260%. A more preferred length is about 3 inches to about 4 inches and an elongation of about 125% to about 200%. A preferred relaxed width is about ¼ inch to about 1½ inches, and a more preferred width is about ½ inch to about 1 inch.

As a percentage of total garment length, the relaxed, attached elastic 88 has a length of about 10% to 100% of total garment length. A preferred length is about 10% to about 50%, and a more preferred length is about 15% to about 25%.

As with waist elastics 68, 70, leg elastics 88 do not necessarily need to be a single ribbon of elastic material, but can be multiple strands of ropes or ribbons of elastic material. If elastics 88 are rope-like, preferred diameters are between about 0.04 inches to about 0.25 inches.

Figure 5B:
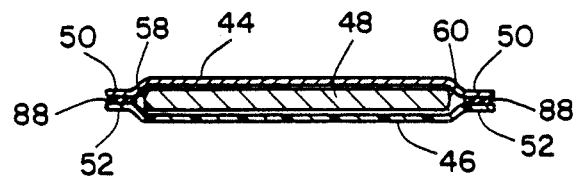
FIG. 5B is a sectional view of FIG. 5A taken along line 5B—5B.

Referring to FIG. 5B, leg elastics 88 are positioned between longitudinal edge portions 50 of bodyside liner 44 and longitudinal edge portions 52 of outer cover 46. Leg elastics 88 can abut against or be spaced apart from respective absorbent sides 58, 60.

Figure 5C:
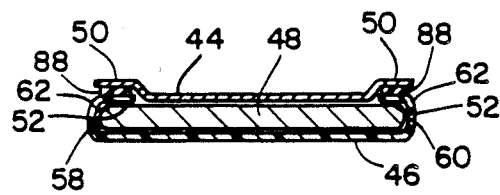
FIG. 5C illustrates a modification of the view in FIG. 5B.

FIG. 5C illustrates a modification of the placement of leg elastics 88. In this modification, outer cover 46 is wrapped around absorbent edges 58, 60 so as to overlap and form baffles 62. Leg elastics 88 are then positioned on top of baffles 62, which are also longitudinal edge portions 52, and bodyside liner 44 is then disposed over leg elastics 88.

Figure 5D:
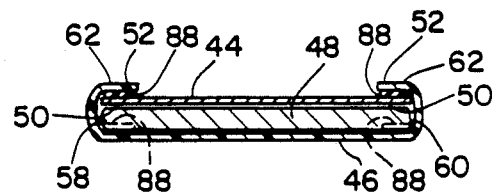
FIG. 5D illustrates another modification of the view of FIG. 5B.

Similarly, FIG. 5D illustrates leg elastics being positioned on top of longitudinal edge portions 50 of bodyside liner 44, and with outer cover 46 then overlapping leg elastics 88 to form baffles 62.

Also, in both the modifications illustrated in FIGS. 5C and 5D, leg elastics 88 may be positioned below absorbent medium 48, as illustrated in dashed lines in FIG. 5D. In this case, leg elastics 88 would be positioned between outer cover 46 and absorbent medium 48. In FIG. 5B, leg elastics 88 can also be positioned either above or below absorbent medium 48.

When leg elastics 88 are used with garment 2, elastic side panel 6 will comprise two elastic side sections 90, 92 (FIG. 5A) and elastic side panel 8 will comprise elastic side sections 94, 96. With the modification of absorbent garment 2 illustrated in FIG. 5A being symmetric about both its longitudinal and transverse axes, each elastic side section 90, 92, 94, 96 will be identical in dimensions. In this particular case where absorbent garment 2 is symmetrical about its axes, a description of only elastic side section 90 will be made since the other side sections 92, 94, 96 are identical. Elastic side section 90 includes a remote edge 24, panel inner side 54, waist end 98 and arcuate side 100. Generally, the length of remote edge 24 is a function of the total garment length. For example, a desired length of remote edge 24 is about 5% to about 50% of the total garment length, a preferred length is about 15% to about 40% of the total garment length, and a more preferred length is about 30% to about 40% of the total garment length.

In the previous paragraph, the modification to absorbent garment 2 of FIG. 5A was described as being symmetric about its longitudinal and transverse axes. However, the present invention contemplates that the construction of the front portion of absorbent garment 2 may differ from the construction of its back portion. Accordingly, for purposes of explanation, it will be assumed that the left portion of absorbent garment 2 illustrated in FIG. 5A is the front portion, and the right portion of Figure 5A is the back portion. In this particular case, elastic side sections 90, 94 will be identical to each other, but different from elastic side sections 92, 96, which in turn will be identical to each other. In this modification of garment 2 in FIG. 5A, sections 90, 94 and sections 92, 96 can take any size or configuration as necessary or desired within the above parameters. Generally speaking, the back portion, i.e., sections 92, 96, will be of greater surface area than sections 90, 94.

The present invention also contemplates the use of both intermediate portions 22 with leg elastics 88 in a suitable positional relationship. For example, portions 22 and elastics 88 can overlap, abut at their edges, or be spaced apart.

Figure 15:
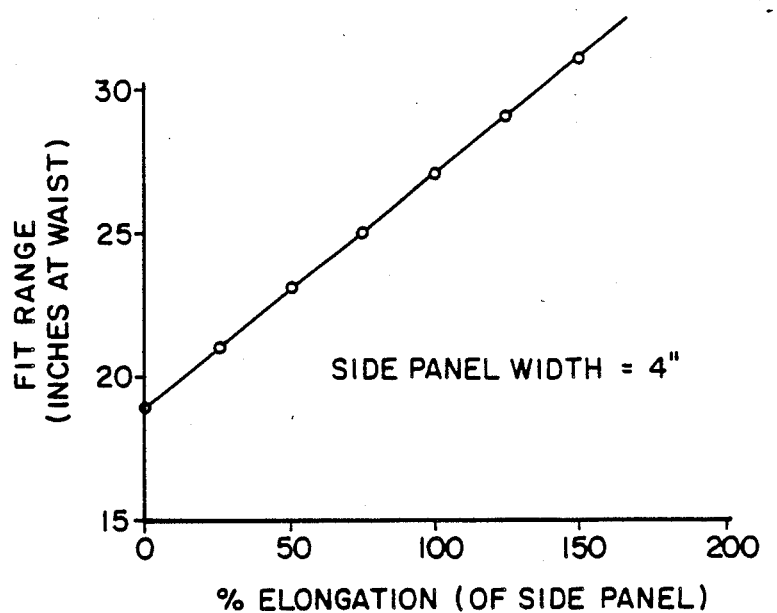
FIG. 15 is a graph of percent elongation of a side panel versus fit range of the waist in inches.

As explained above, absorbent garment 2 is designed to fit a large range of sizes merely by changing the dimensions of elastic side panels 6, 8, or by changing the type of elastic material of which side panels 6, 8 are made. Generally, the range of sizes can be varied by (1) selecting a material having a desired modulus of elasticity, and/or (2) increasing the length and width dimensions of a given elastic material of which side panels 6, 8 are made. Side panels 6, 8 will generally have a width of about ½ inch to 5 inches, and will be made of a material having an elongation or elasticity from about 10% to about 500%. Preferably, side panels 6, 8 will have a width from about 2 inches to about 3½ inches, and the material of which they are made will have an elasticity between about 50% to about 300%. In a more preferred embodiment, side panels 6, 8 will have a width of about 1½ inches to about 2 inches, and an elasticity from about 75% to Referring to FIGS. 15-17, the relationships between side panels 6, 8 and the range of fit sizes of absorbent garment 2 are graphically illustrated. In FIG. 15, each side panel 6, 8 has a width of about 4 inches, and the percent elongation of the side panels is plotted against the fit range in inches at the waist. As illustrated, there is a general linear relationship between the percent elongation of the elastic material of which side panels 6, 8 are made and the size range of the waist measured in inches.

Figure 16:
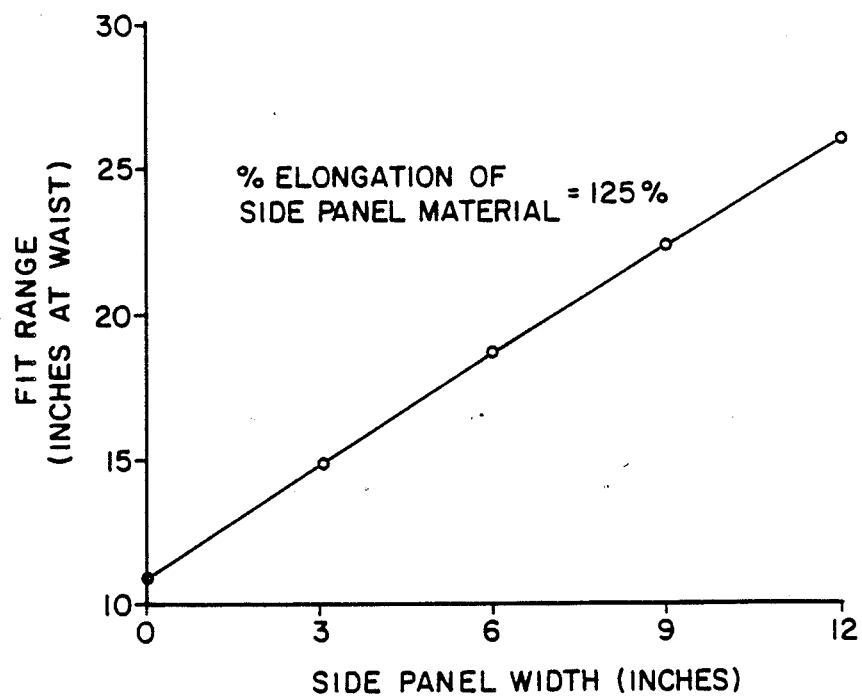
FIG. 16 is a graph of the side panel width in inches versus the fit range at the waist in inches.

FIG. 16 illustrates the relationship between side panel width and the fit range in inches at the waist for an elastic material having a percent elongation of 125%. As illustrated, there is a general linear relationship between an increase in the side panel width in inches versus the fit range in inches at the waist.

Figure 17:
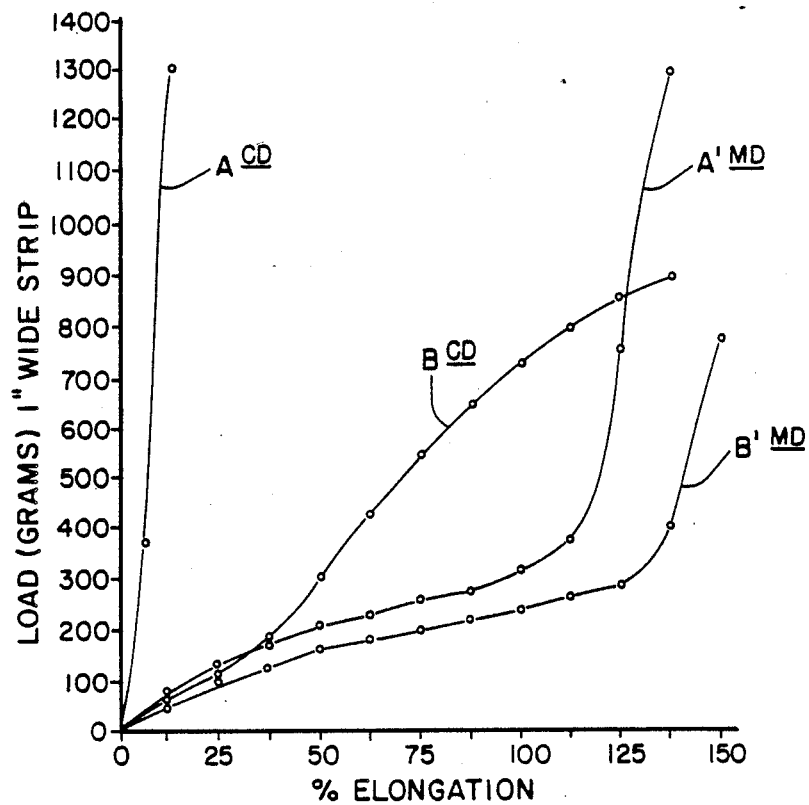
FIG. 17 is a graph of percent elongation versus the load in grams for a one inch wide strip of side elastic.

FIG. 17 is a graph plotting percent elongation versus the load in grams on a 1 inch wide strip of elastic material. The load in grams measures the tension at elongation of the particular material, and this feature is maximized by theoretically having a slope of zero for each plot. In FIG. 17, the plotted curves represent 2 elastic materials, wherein curve A represents the cross-direction stretch and curve A' represents the machine-direction stretch of one material; and curve B represents the cross-direction stretch and curve B' represents the machine-direction stretch of the other material. The machine direction stretch, preferably in the stretch-bonded laminate embodiment, is the force vector applied horizontally inwardly toward the hips and mid-section of the garment when worn. This stretch-strain relationship is important to the use and performance of the garment. The side panel material must stretch to adjust to various sizes. The tension cannot be so high that the garment is difficult to use or be too tight during use. Nor, can it be so low in tension as not to maintain the product in position during use. Preferably, the materials of which side panels 6, 8 are made will have a tension range, load (grams) per 1-inch wide strips, from 50 grams to 1,000 grams. In a more preferred embodiment, the side panel materials would have a tension range of about 200 to about 500 grams per 1-inch wide strip. Secondly, curves A' and B' both illustrate relatively very gradual slopes between 0 and about 125% elongation. The slope is important to maintain a constant fit tension at the various sizes. With a theoretical slope of 0, the tension of the product would be the same at the relaxed size as it would be at the fully-stretched size.

Figure 18:
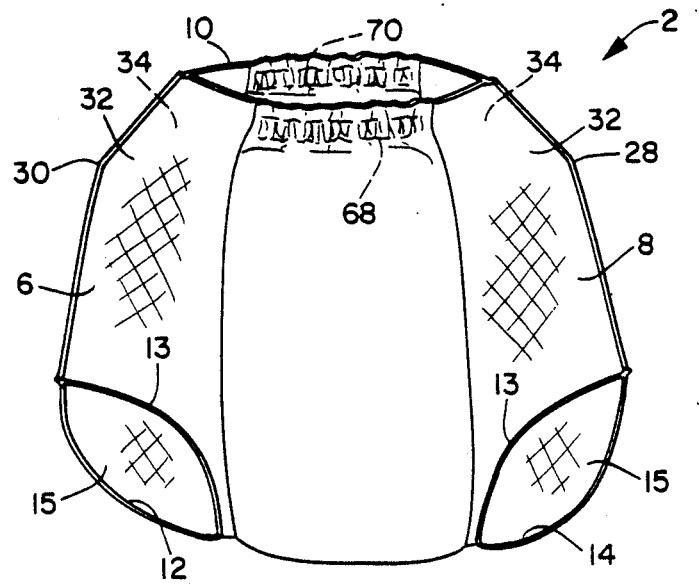
FIG. 18 illustrates yet another pant or garment.

Referring now to FIG. 18, there is yet another modification of absorbent garment 2 that includes waist elastics 68, 70. A unique feature of this modification of absorbent garment 2 is the geometry of elastic side panels 6, 8. Specifically, it can be seen that the front portions 13 of leg openings 12, 14 are cut higher than the back portions 15 of leg openings 12, 14. The purpose for this particular geometry of leg openings 12, 14 is to improve further the fit of the garment. The added material in the back provides coverage of the buttocks, while in the front the cut is higher in following the curvature of the leg, thereby permitting freer leg movement.

The upper portions of elastic side panels 6, 8 are identified as remote end segments 32, 34, and they are cut so that they slope inwardly and upwardly from the intermediate portions of side panels 6, 8 toward waist opening 10. The purpose for this is to improve further the fit of the garment, especially when the user is disproportionate at the hips and waist. The design or configuration also assists in pulling the garment up in place. The length of each sloping end segment 32, 34 is from about 3% to about 40% of the total garment length, preferably about 5% to about 25% of total garment length, and more preferably about 10% to about 15% of total garment length.

The angular slope, as measured with the vertical in Figure 18, of end segments 32, 34 is from about 5° to about 55°, preferably from about 10° to about 40°, and more preferably from 15° to about 30°.

Figure 14:
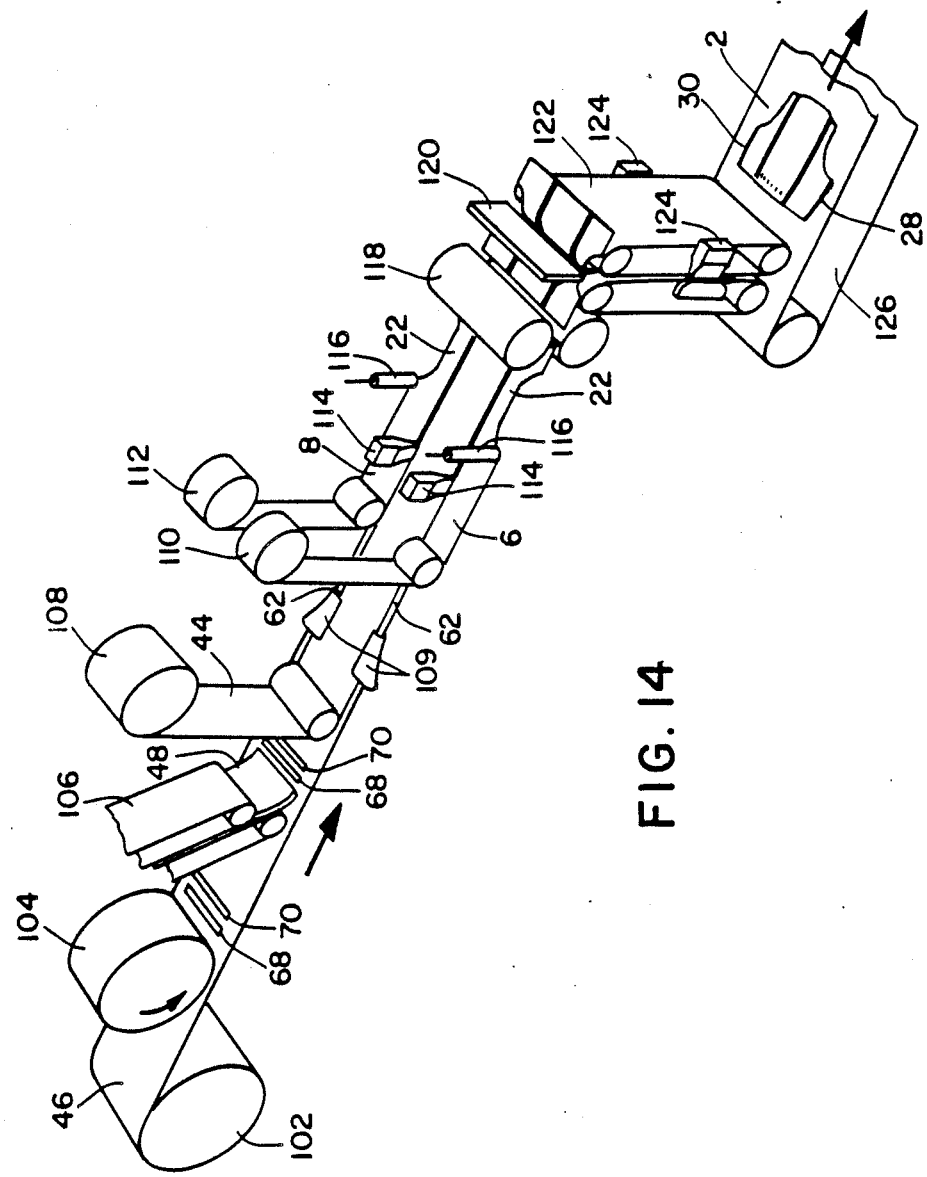
FIG. 14 is a schematic of one apparatus for producing one embodiment of a pant or garment.

Referring now to FIG. 14, a description will be made of one process for making one embodiment of a pant or garment. Supply roll 102 provides a continuous supply of outer cover 46 to supply drum 104, which attaches, if desired, waist elastics 68, 70 thereon. After application of waist elastics 68, 70, outer cover 46 continues to conveyor assembly 106 which positions absorbent medium 48 between waist elastics 68, 70. Thereafter, supply roll 108 delivers a continuous supply of bodyside liner 44 on top of waist elastics 68, 70, absorbent mediums 48 and the continuous supply of outer cover 46. Folding bars 109 then fold outer cover 46, which has a width greater than the width of absorbent medium 48 and bodyside liner 44, over mediums 48 and liner 44 to form baffles 62. After baffles 62 have been formed, supply rolls 110, 112 provide a continuous supply of elastic side panels 6, 8, and bonding station 114 then bonds, such as by ultrasonic, thermal, or adhesive bonding, elastic side panels 6, 8, bodyside liner 44 and outer cover 46. Leg cut-out station 116, which can be pressurized fluid-jets or a rotary die cutter, then cuts side panels 6, 8 to form intermediate portions 22. As the composite continues through the process, cutting station 118 severs the composite between waist elastics 68, 70, the composite is then tucked or folded in half by tucker bar 120, which contacts an intermediate portion of a severed composite and moves it between the individual conveyors of conveyor assembly 122. Located in conjunction with conveyor assembly 122 is seam bonding station 124 which bonds, such as by ultrasonic, thermal, or adhesive bonding, elastic side panels 6, 8 to form seams 28, 30 of absorbent garment 2. Conveyor assembly 122 then delivers absorbent garment 2 to transfer conveyor assembly 126, which delivers absorbent garments 2 to the next handling station.

The process illustrated in FIG. 14 can be easily adapted to make other embodiments such as those illustrated in FIG. 5A and FIG. 18, and other constructions such as those illustrated in FIGS. 8-10.

While this invention has been described as having preferred embodiments, it will be understood that it is capable of further modifications. This application is therefore intended to cover any variations, uses or adaptations of the invention following the general principles thereof, and including such departures from the present disclosure as come within known or customary practice in the art to which this invention pertains and fall within the limits of the appended claims.

What is claimed is:

1. A seam construction in a disposable absorbent article, comprising:
   a layered composite portion comprising a liquid pervious top layer, an absorbent middle layer, and a liquid impervious bottom layer, and
   stretchable members being joined to said layered composite portion between respective opposite longitudinal side portions of said liquid pervious top layer and said liquid impervious bottom layer, said stretchable members also extending outwardly beyond said opposite longitudinal side portions of said top and said bottom layers, whereby said layered composite portion and said stretchable members form a seam construction that is resistant to liquid leakage and that provides a gentle transition between said layered composite portion and said stretchable members.

2. A seam construction in a disposable absorbent article, comprising:
- a layered composite portion comprising a liquid pervious top layer, a liquid impervious bottom layer, and an absorbent middle layer,
- stretchable members being joined to said layered composite portion between respective side portions of said liquid pervious top layer and said liquid impervious bottom layer,
- said stretchable members extending outwardly beyond said side portions of said top and said bottom layers.

3. A seam construction in a disposable absorbent article, comprising:
- a layered composite portion comprising a liquid pervious top layer, a liquid impervious bottom layer, and an absorbent middle layer,
- edge portions of said liquid impervious bottom layer overlapping at least partially with said absorbent middle layer and said liquid pervious top layer, and
- stretchable members being joined to said layered composite portion and extending outwardly beyond said edge portions.

4. A seam construction in a disposable absorbent article, comprising:
- a layered composite portion comprising a liquid pervious top layer, a liquid impervious bottom layer, and an absorbent middle layer,
- edge portions of said liquid impervious bottom layer overlapping at least partially said absorbent middle layer, and
- stretchable members being joined to said layered composite portion and extending outwardly beyond said edge portions.

5. A disposable pant-like garment for absorbing human discharge, comprising:
- an absorbent assembly comprising a liquid impervious outer cover, a liquid pervious liner, and an absorbent medium therebetween,
- stretchable side panels forming with said absorbent assembly a waist opening and a pair of leg openings,
- an edge portion of at least one of said stretchable side panels being joined between respective edge portions of said outer cover and said liner, and
- a remaining portion of said at least one stretchable side panel extending outwardly beyond said outer cover and said liner.

6. The seam of claim 1 or 2 wherein said stretchable members have an elasticity from about 10% to about 500%.

7. The seam of claim 1 or 2 wherein said stretchable members are made of a material having a tension range from about 50 grams to about 1,000 grams per inch.

8. The seam of claim 1 or 2 wherein said stretchable members overlap said middle layer.

9. The seam of claim 8 wherein each said stretchable member overlaps from about 0% to about 50% with said middle layer.

10. The seam of claim 9 wherein each said stretchable member overlaps from about 3% to about 20% with said middle layer.

11. The seam of claim 10 wherein each said stretchable member overlaps from about 6% to about 12% with said middle layer.

12. A seam construction in an absorbent article, comprising:
- a layered composite portion comprising a liquid pervious top layer an absorbent middle layer, and a liquid impervious bottom layer,
- longitudinal edge portions of said liquid impervious bottom layer overlapping at least partially with said absorbent middle layer and said liquid pervious top layer, and
- stretchable members having joined to said layered composite portion,
- whereby said layered composite portion and said stretchable members form a seam construction that is resistant to liquid leakage.

13. The seam of claim 12 or 3 wherein said edge portions overlap from about 0% to about 99% of said middle layer.

14. The seam of claim 13 wherein said edge portions overlap from about 10% to about 50% of said middle layer.

15. The seam of claim 14 wherein said edge portions overlap from about 10% to about 20% of said middle layer.

16. The seam of claim 12 or 3 wherein said stretchable members overlap said middle layer.

17. The seam of claim 16 wherein each said stretchable member overlaps from about 0% to about 50% with said middle layer.

18. A seam construction in an absorbent article, comprising:
- a layered composite portion comprising a liquid pervious top layer, an absorbent middle layer, and a liquid impervious bottom layer,
- longitudinal edge portions of said liquid impervious bottom layer overlapping at lease partially said absorbent middle layer, and
- stretchable members being joined to said layered composite portion,
- whereby said layered composite portion and said stretchable members form s seam construction resistant to liquid leakage.

19. The claim of claim 18 or 4 wherein said liquid pervious top layer overlaps said edge portions of said liquid impervious bottom layer.

20. The seam of claim 19 wherein said edge portions of said liquid impervious bottom layer overlap from about 0% to about 99% with said middle layer.

21. The seam of claim 20 wherein each said stretchable member overlaps from about 0% to about 50% with said middle layer.

22. A disposable pant-like garment for absorbing human discharge, comprising:
- an absorbent assembly comprising a liquid impervious outer cover, a liquid impervious liner, and an absorbent medium therebetween;
- stretchable side panels forming with said absorbent assembly a waist opening and a pair of leg openings;
- an edge portion of at least one of said stretchable side panels being joined between respective longitudinal edge portions of said outer cover and said liner, and
- a remaining portion of said at least one stretchable side panel extending outwardly beyond said outer cover and said liner thereby forming a seam construction that is resistant to liquid leakage and that provides a gentle transition between said absorbent assembly and said stretchable side panels.

23. The garment of claim 22 or 5 wherein each said edge portion of a respective said stretchable side panel abuts directly against a respective edge of said absorbent medium.

24. The garment of claim 22 or 5 wherein each said edge portion or a respective said stretchable side panel is spaced apart from a respective edge of said absorbent medium from about 0 inches to about 2 inches.

25. The garment of claim 22 or 5 wherein said stretchable side panels have an elasticity from about 10% to about 500%.

26. The garment of claim 22 or 5 wherein said stretchable side panels have a tension range from about 50 grams to about 1,000 grams per inch.

27. The garment of claim 22 or 5 further comprising a waist elastic member at lease at one end of said absorbent assembly and disposed between said outer cover and said liner.

28. The garment of claim 27 wherein said waist elastic member comprises a plurality of waist elastic elements.

29. The garment of claim 27 wherein opposite ends of said waist elastic member abut directly against respective ones of said edge portions of said stretchable side panels to from a substantially continuous elastic effect about said waist opening.

30. The garment of claim 27 wherein opposite ends of said waist elastic members are spaced apart from respective ones of said edge portions of said stretchable side panels from about 0 inches to about 2 inches.

31. The garment of claim 27 wherein said waist elastic members overlap with said stretchable side panels.

32. The seam of claim 1 or 2 wherein said stretchable members abut directly against respective opposite side edges of said middle layer.

33. The seam of claim 1 or 2 wherein said stretchable members are spaced apart from respective opposite side edges of said middle layer a distance from about 0 inches to about 2 inches.

34. The seam of claim 33 wherein said stretchable members are spaced apart from respective said opposite side edges from about 0 inches to about 1 inch.

35. The seam of claim 34 wherein said stretchable members are spaced apart from respective said opposite side edges from about 0 inches to about $\frac{1}{2}$ inch.

36. A disposable pant-like garment for absorbing human discharge, comprising:
   an absorbent assembly comprising a liquid impervious bottom layer, a liquid pervious top layer, and an absorbent middle layer,
   an edge portion of said liquid impervious bottom layer overlapping at least partially with said absorbent middle layer and said liquid pervious top layer, and
   stretchable side panels forming with said absorbent assembly a waist opening and a pair of leg openings.

37. A disposable pant-like garment for absorbing human discharge, comprising:
   an absorbent assembly comprising a liquid impervious bottom layer, a liquid pervious top layer, and an absorbent middle layer,
   an edge portion of said liquid impervious bottom layer overlapping at least partially with said absorbent middle layer, and
   stretchable side panels forming with said absorbent assembly a waist opening and a pair of leg openings.

* * * * *

UNITED STATES PATENT AND TRADEMARK OFFICE
CERTIFICATE OF CORRECTION

PATENT NO. : 4,938,753

DATED : July 3, 1990

INVENTOR(S) : Paul T. Van Gompel; Jody D. Suprise; Robert J. Schleinz

It is certified that error appears in the above-identified patent and that said Letters Patent is hereby corrected as shown below:

Column 1, line 12, delete the word "child'" and insert therefor --child's--.

Column 2, line 31, begin a new paragraph after "FIG. 1;".

Column 2, line 32, begin a new paragraph after "FIG. 1A;".

Column 2, line 33, begin a new paragraph after "FIG. 1;".

Column 2, line 38, begin a new paragraph after "joined;".

Column 6, line 58, add the words "3% to about 20%, and more preferably about 6% to about" after the word "about".

Column 7, line 8, delete the word "FIG." and substitute therefor --FIGS.--.

Column 10, line 60, add the words "about 200%." after the word "to".

Column 12, line 2, add the word "about" after the word "from".

Claim 1, column 12, line 52, delete the words "a disposable" and insert therefor --an--.

Claim 12, column 14, line 8, delete the word "having" and insert therefor --being--.

UNITED STATES PATENT AND TRADEMARK OFFICE
CERTIFICATE OF CORRECTION

PATENT NO. : 4,938,753
DATED : July 3, 1990
INVENTOR(S) : Paul T. Van Gompel; Jody D. Suprise; Robert J. Schleinz It is certified that error appears in the above-identified patent and that said Letters Patent is hereby corrected as shown below:

Claim 18, column 14, line 38, delete the word "s" after the word "form" and insert therefor --a--.

Claim 22, column 14, line 52, delete the word "impervious" and insert therefor --pervious--.

Claim 22, column 14, line 63, insert "," after the word "liner".

Claim 24, column 15, line 4, delete the word "or" and insert therefor --of--.

Claim 27, column 15, line 15, delete the word "lease" and insert therefor --least--.

Signed and Sealed this

Thirty-first Day of March, 1992

Attest:

HARRY F. MANBECK, JR.

*Attesting Officer*  *Commissioner of Patents and Trademarks*